(12) United States Patent
Ni et al.

(10) Patent No.: US 10,161,904 B2
(45) Date of Patent: Dec. 25, 2018

(54) METHOD FOR TRACING DISTRIBUTION OF MOVING IONS IN ION MOBILITY SPECTROMETER

(71) Applicant: Graduate School at Shenzhen, Tsinghua University, Shenzhen, Guangdong (CN)

(72) Inventors: Kai Ni, Guangdong (CN); Kaitai Guo, Guangdong (CN); Quan Yu, Guangdong (CN); Binchao Tang, Guangdong (CN); Zhou Yu, Guangdong (CN); Xiang Qian, Guangdong (CN); Xiaohao Wang, Guangdong (CN)

(73) Assignee: GRADUATE SCHOOL AT SHENZHEN, TSINGHUA UNIVERSITY, Shenzhen, Guangdong (CN)

( * ) Notice: Subject to any disclaimer, the term of this patent is extended or adjusted under 35 U.S.C. 154(b) by 0 days.

(21) Appl. No.: 15/486,040

(22) Filed: Apr. 12, 2017

(65) Prior Publication Data
US 2017/0219524 A1 Aug. 3, 2017

Related U.S. Application Data

(63) Continuation of application No. PCT/CN2016/086617, filed on Jun. 21, 2016.

(30) Foreign Application Priority Data

Dec. 15, 2015 (CN) .......................... 2015 1 0934309

(51) Int. Cl.
*G01N 27/62* (2006.01)
*G01N 21/64* (2006.01)

(52) U.S. Cl.
CPC ....... *G01N 27/622* (2013.01); *G01N 21/6428* (2013.01); *G01N 21/6402* (2013.01)

(58) Field of Classification Search
CPC ............. G01N 37/622; G01N 21/6492; G01N 21/6404; G01N 21/6428; C07B 57/00; C07B 63/00
See application file for complete search history.

(56) References Cited

U.S. PATENT DOCUMENTS

| 4,352,674 A | 10/1982 | Fery |
| 6,144,029 A | 11/2000 | Adler |

(Continued)

FOREIGN PATENT DOCUMENTS

| CN | 1639565 | 7/2005 |
| CN | 104054156 | 9/2014 |

(Continued)

OTHER PUBLICATIONS

Office Action issued in Chinese Application No. CN201510934309.2 dated Sep. 1, 2017, 5 pages provided.

(Continued)

*Primary Examiner* — Eliza Osenbaugh-Stewart
(74) *Attorney, Agent, or Firm* — Hamre, Schumann, Mueller & Larson, P.C.

(57) ABSTRACT

A method for tracing a distribution of moving ions in an ion mobility spectrometer is provided, including steps: first selecting a sample having light-emitting characteristics as a tracing sample; subsequently, ionizing the tracing sample by using an ionization source, and feeding ions of the tracing sample to a drift tube of the ion mobility spectrometer; using a plate to collect the ions at a cross section to be detected; and finally processing the ions collected on the plate by using an appropriate means, thereby enabling the ions to emit light, and displaying a distribution view of movement (Continued)

positions of the ions on the cross section. By combining a light-emitting tracing means and movements of charged ions in an ion mobility spectrometer, it is able to master a position distribution of the charged ions in the ion mobility spectrometer more intuitively and practically.

**7 Claims, 3 Drawing Sheets
(1 of 3 Drawing Sheet(s) Filed in Color)**

(56) References Cited

U.S. PATENT DOCUMENTS

| | | |
|---|---|---|
| 2005/0116160 A1 | 6/2005 | Guevremont |
| 2008/0173809 A1* | 7/2008 | Wu .......................... C07B 63/00 250/283 |
| 2009/0218481 A1* | 9/2009 | DeWalch ................ G01N 21/53 250/281 |
| 2013/0306855 A1* | 11/2013 | Raptakis ............... H01J 49/025 250/282 |
| 2014/0319343 A1 | 10/2014 | Pawlowicz et al. |

FOREIGN PATENT DOCUMENTS

| | | |
|---|---|---|
| CN | 203929711 U | 11/2014 |
| CN | 105403614 | 3/2016 |
| WO | 2015179709 A1 | 11/2015 |

OTHER PUBLICATIONS

International Search Report and Written Opinion issued in PCT/CN2016/086617 dated Sep. 27, 2016, 13 pages.

* cited by examiner

METHOD FOR TRACING DISTRIBUTION OF MOVING IONS IN ION MOBILITY SPECTROMETER

CROSS REFERENCE TO RELATED APPLICATIONS

This application is a continuation application of PCT/CN2016/086617, filed on Jun. 21, 2016. The contents of PCT/CN2016/086617 are all hereby incorporated by reference.

BACKGROUND

Technical Field

The present application relates to an ion mobility spectrometer, and in particular to a method for tracing a distribution of moving ions in an ion mobility spectrometer.

Related Art

A movement problem of a sample ion in a drift tube is an important component of analyzing an ion mobility spectrometer, and is basis of designing the ion mobility spectrometer, exploring performances, and detecting effects.

At present, when exploring a movement of the sample ion in the ion mobility spectrometer, often a mathematical model of the ion mobility spectrometer is first established and a possible moving track of the ion is calculated according to a theoretical formula. Today, computer performances are promoted. Various ion movement simulation software of the ion mobility spectrometer such as SIMION (a simulation software for electrostatic lens analysis) are frequently used, and a researcher may quickly and conveniently establish an electric field model in the ion mobility spectrometer by using a computer, so as to give an initial velocity and a charging amount to a particular sample ion to generate a corresponding cross sectional distribution view of the moving track of the ion. However, differences exist between the theory and the reality. The cross sectional distribution view of the moving track of the ion which is theoretically obtained only has guiding significance for the design and performances of the ion mobility spectrometer.

A Faraday plate cooperating with a micro-current amplifier is an ion detection method at an atmospheric pressure. This method generates a reaction current by using neutralization of charged ions on a surface of the Faraday plate, so as to be converted into a voltage signal by the micro-current amplifier. This ion detection system often is placed at a tail end of the ion mobility spectrometer. However, in actual applications, if the Faraday plate is placed in the drift tube, an existing electric field is affected, and only a total current caused by impacting the ions at the surface of the Faraday plate at the same time is detected.

SUMMARY

An objective of the present application is for resolving a problem at the present that a movement of charged ions in an ion mobility spectrometer can only be emulated and simulated according to a theoretical calculation, so as to simply and conveniently detect a position of the charged ions in the ion mobility spectrometer.

For this purpose, the present application provides a method for tracing a distribution of moving ions in an ion mobility spectrometer. The method includes the following steps: a step of selecting an ion sample of using a sample having light-emitting characteristics as a tracing sample of the ion mobility spectrometer; a step of ionization sampling (also be called ion processing) of acting on the tracing sample by using an ionization method which does not affect the light-emitting characteristics of the tracing sample, thereby enabling ions of the tracing sample to reach a standard for representing a condition of an original moving track of the ions under an action of the ion mobility spectrometer, and feeding the ions of the tracing sample into a drift tube of an ion mobility spectrometer to be drifted; a collection step of collecting the ions of the tracing sample by using an ion collecting and developing plate which does not affect (using a non-conductive material as an example) the ion mobility spectrometer at a cross section of movements of the ions of the tracing sample; and a developing step of making light-emitting the ions of the tracing sample collected on the ion collecting and developing plate by means of an optical means emit light, so as to obtain an ion distribution state on the cross section.

The ion mobility spectrometer refers to a micro substance detecting instrument which separates and determines ions by using a difference between drift times of the ions.

The light-emitting characteristics in the step of selecting an ion sample refer to that a substance has a characteristic of releases energy by means of light during a process of returning to a ground state after being excited to absorb energy to be drifted to an excited state (an unsteady state).

The ionization method which acts on the tracing sample and does not affect the light-emitting characteristics of the tracing sample in the step of ionization sampling (ion processing) includes an electrospray ionization source, an ultraviolet lamp ionization source, a matrix-assisted laser desorption ionization source, and a chemical ionization.

The cross section of the ions of the tracing sample in the collection step may be a to-be-analyzed section of the drift tube of the ion mobility spectrometer that is vertical to a movement direction of the ions; and a specific measurement position may be determined according to the requirements.

The ion collecting and developing plate in the collection step refers to a plate which does not affect an electric field distribution of the ion mobility spectrometer and has a special shape design, including a microporous paper plate, a microporous glass plate, and a microporous rubber plate.

The optical means in the developing step refers to illuminating, by using exciting light meeting an excitation wavelength of the ions of the tracing sample, the ions of the tracing sample collected on the ion collecting and developing plate to enable the ions of the tracing sample to emit light-emitting photons. A diagram about light-emitting positions is obtained at a surface of the ion collecting and developing plate.

The present application proposes combining a light-emitting tracing means and movements of charged ions in an ion mobility spectrometer, so as to master a position distribution of the charged ions in the ion mobility spectrometer more intuitively and practically.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A is a developed pattern, FIG. 2B is an X-Y plane distribution diagram, FIG. 2C is a diagram of axes of X, Y. and Z. and axes X and Y in FIG. 2C are position axes using pixel sizes as units, and axis Z and a grey scale correspondingly received ions quantities.

DETAILED DESCRIPTION

The following further describes the present application with reference to the accompanying drawings and the preferred implementation manners.

Light-emitting tracing is a characterization means and a display method which may be applied to a bioprobe, wastewater treatment, heavy metal tracing, and alkalinity acidity detection. By labeling a luminescent dye on a detected object, and illuminating a sample by a particular wave band, the sample marked the luminescent dye emits light different from an excitation wave band so as to display the sample of the marked object. However, there are a lot of problems to be resolved when applying the light-emitting tracing to tracing a distribution of moving ions in an ion mobility spectrometer. This is described in detail below in the embodiments.

Embodiment 1

Figure 1:
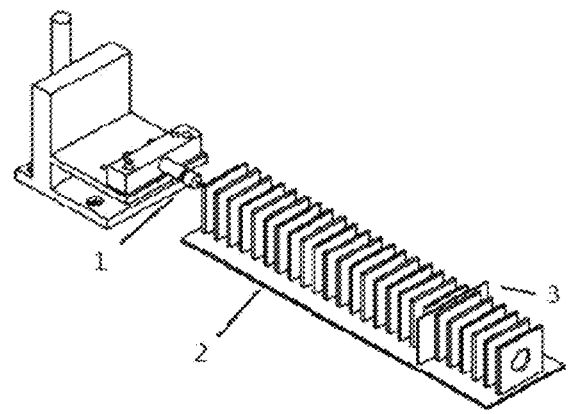
FIG. 1 is a structural diagram of an ion mobility spectrometer in a specific implementation manner of the present application.

FIG. 1 is a structural diagram of an ion mobility spectrometer in a specific implementation manner of the present application, where 1 represents an electrospray ionization source, 2 represents a drift tube, and 3 represents an ion collecting and developing plate.

Embodiment 1 includes the followings steps:

(1) Select RHODAMINE 6G (Shanghai Jingchun Biochemical Co., Ltd.) (fluorescence) having light-emitting characteristics as a tracing sample distributed at a cross section of a drift tube of the ion mobility spectrometer. The RHODAMINE 6G is a flavovirens luminescent dye which is soluble in an aqueous solvent such as water or methanol. The electrospray ion mobility spectrometer is a detection means of changing a liquid sample into gaseous charged ions by applying a high-voltage electric field, and then entering a drift region having an even electric field, so as to determine a nature of an ion separation according to a time for the ions to pass through the drift region. The drift region plays a pivotal role during the process of separating a sample. Therefore, when verifying a transmission efficiency of the charged ions in the ion mobility spectrometer, a simple and practical method is urgently needed, so as to detect a distribution state of ion transmission at the cross section and a moving track of the ions without bringing in an external interference.

(2) Prepare a methanol solution with a concentration of 5 µM of the RHODAMINE 6G (Shanghai Jingchun Biochemical Co., Ltd.). A sampling syringe (series Hamilton 1700) is used to load the methanol solution with a concentration of 5 µM of the RHODAMINE 6G. At a front end of the sampling syringe, capillary tubes with internal diameters of 75 µm are bilaterally connected in serial by using a PEEK material, and a voltage being 6000 V higher than a maximum voltage of the drift region of the ion mobility spectrometer is applied thereto. A high-potential methanol solution of the RHODAMINE 6G forms an electrospray with a sampling rate of 5 µL/min at a tip of the serially connected capillary tubes in the sampling syringe and enters the drift tube of the ion mobility spectrometer.

(3) A glass slide whose surface is cleaned by methanol and plasma is used as an ion collecting and developing plate ((hereafter referred to as a plate). Length and width of the plate respectively is 60*20 mm, and thickness thereof is 4 mm. The plate is taken out from the drift tube of the ion mobility spectrometer after being fixed, using an adhesive tape, at the cross section of the drift tube which needs to detect the ion distribution for 40 s. During the period in which the collecting material is placed in the drift tube, the ions of the tracing sample are maintained, in the drift tube of the ion mobility spectrometer, to normally pass through and be captured by the collecting material. The surrounding is not touched during the processes of taking and placing.

(4) A pump laser of a wavelength of 532 nm is used as an excitation light source, and a circular even light spot with a diameter of 50 mm is achieved by expanding by a convex lens. The plate which captures the ions of the tracing sample is taken out and is placed under the light spot. A picture of light spot distribution represented by the light-emitting ions enriched on a collecting paper sheet is obtained by cooperating a long-wave pass filter of a wavelength of 560 nm with a CCD camera. That is, the distribution state of the ions in the interface may be represented.

Figure 2A:
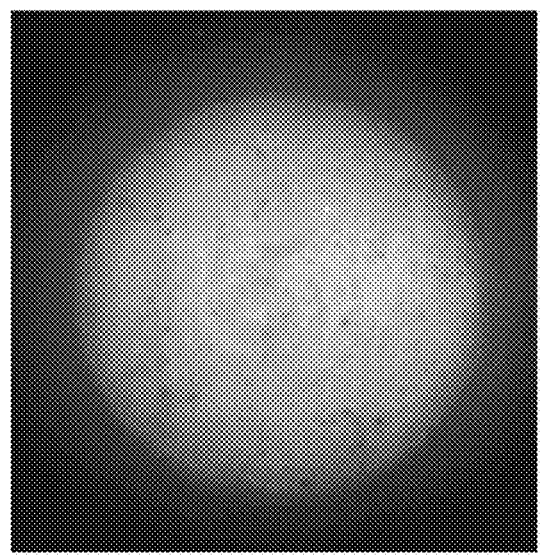
FIG. 2A, FIG. 2B, and FIG. 2C are ion distribution diagrams on a cross section of a drift tube of an ion mobility spectrometer obtained in specific implementation manners of the present application, where
Figure 2B:
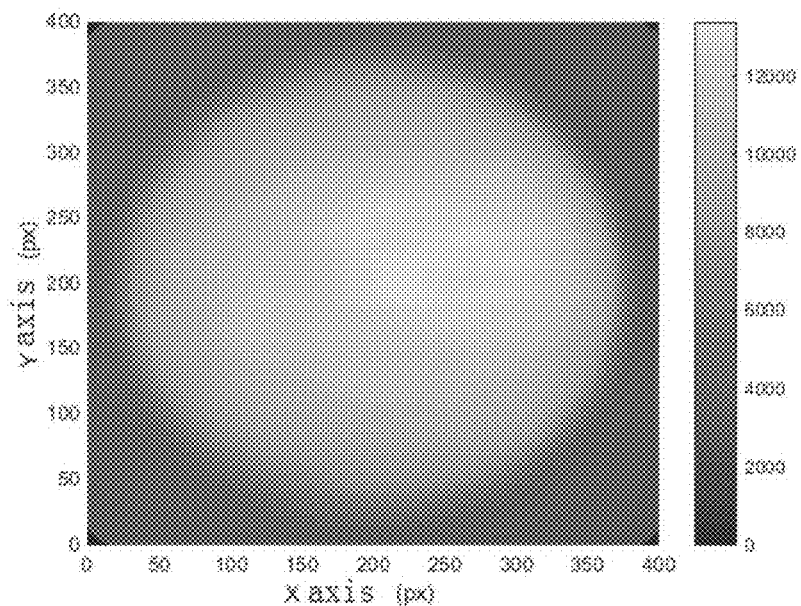
Figure 2C:
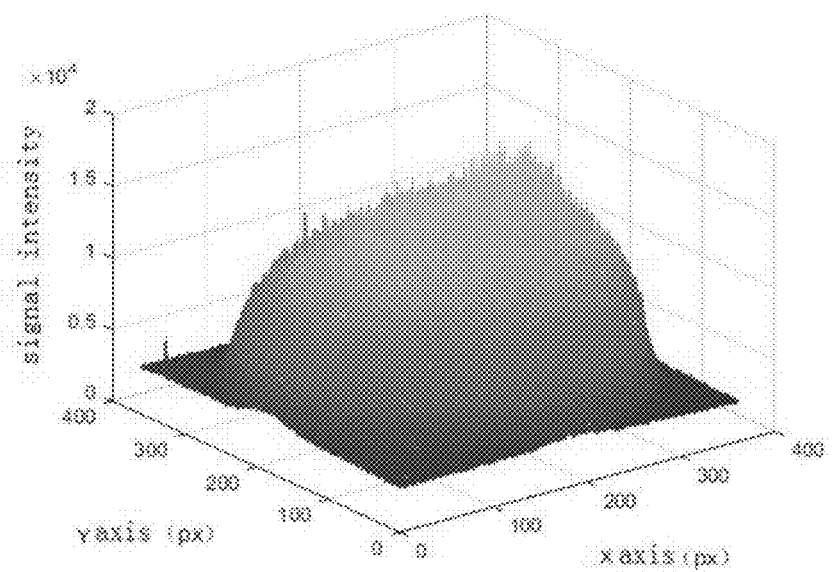

FIG. 2A, FIG. 2B, and FIG. 2C are ion distribution diagrams on a cross section of a drift tube of an ion mobility spectrometer obtained in specific implementation manners of the present application, where a position at which an ionization source is located is the brightest part in the figures, and it is indicated that the ionization source at this time is not at a center of the drift tube. FIG. 2A is a developed pattern, FIG. 2B is an X-Y plane distribution diagram, and FIG. 2C is a diagram of axes of X, Y, and Z.

Figure 3:
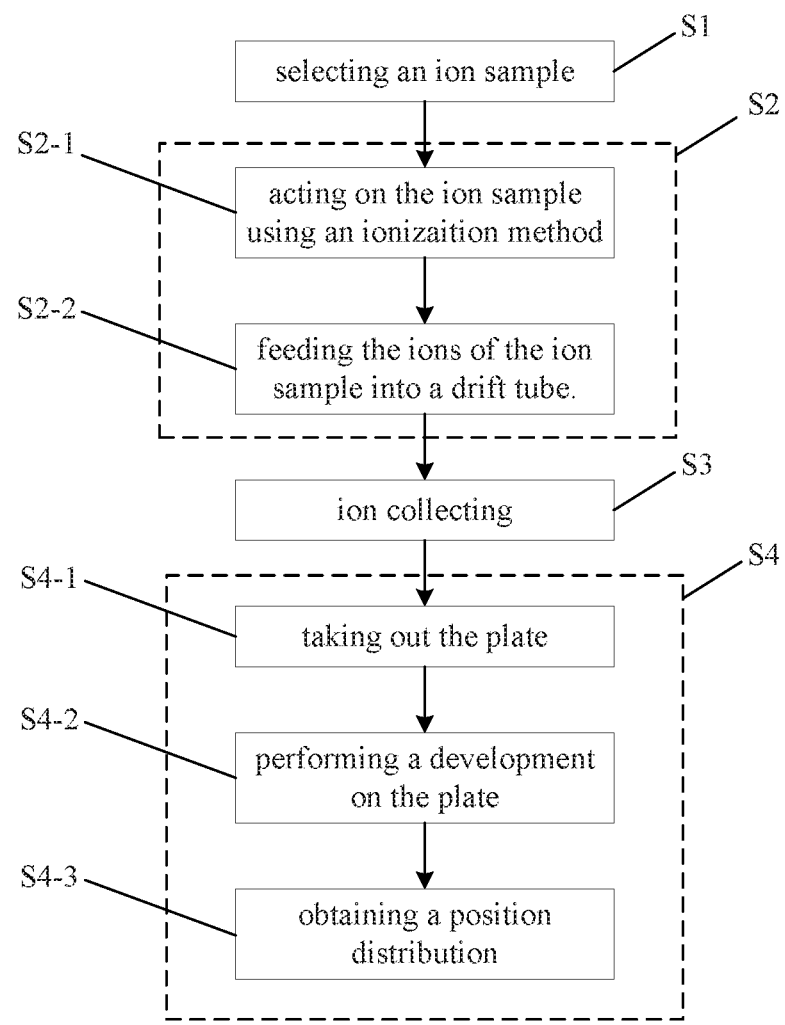
FIG. 3 is a flow diagram of a method for tracing a distribution of moving ions in an ion mobility spectrometer in a specific implementation manner of the present application.

FIG. 3 is a flow diagram of a method for tracing a distribution of moving ions in an ion mobility spectrometer in a specific implementation manner of the present application. As discussed above, the method in an embodiment includes selecting an ion sample S1, ionization sampling S2, ion collecting S3, and development S4. The ionization sampling S2 includes acting on the ion sample using an ionization method S2-1 and feeding the ions of the ion sample into a drift tube S2-2. The development S4 includes taking out the plate S4-1, performing a development on the plate S4-2, and obtaining a position distribution S4-4. Taking out the plate S4-1 is taking out the plate 2 (shown in FIG. 1) from the drift tube 3 (shown in FIG. 1) of the ion mobility spectrometer after the plate 2 has been fixed at a cross section of the drift tube to collect ions of the ion sample for a set period of time in an embodiment. Performing a development on the plate S4-2 includes illuminating the ions collected on the plate 2 with an excitation light source that has a wavelength that excites the ions collected on the plate 2 so that the collected ions on the plate 2 emit light and form a diagram of light-emitting positions of the collected ions on the plate 2.

It should be noted that the ions of the tracing sample may also be other ions having fluorescent or phosphorescent characteristics, having no requirements for charges and masses thereof so long as being replaced by ions of a similar drift rate. In this way, a sectional distribution of the replaced ions may be represented.

The foregoing embodiment uses the electrospray ionization source, but may also use a soft ionization means such as a matrix-assisted laser desorption ionization source, and an ultraviolet lamp ionization source, and a chemical ionization.

If ion reflection or scattering occurs to the ion collecting and developing plate, a measurement result may be affected. Therefore, a developing plate which may fix the ions and avoid diffused reflections of the ions needs to be selected. During an experimental process, a fixed image at an interface of the ion track may be obtained by using the glass slide. Moreover, as a receiving time increases during the experiment, a shape of an image pattern would not change, but brightness changes.

The ion collecting and developing plate in the enrichment (collection) step does not affect an electric field distribution of the ion mobility spectrometer and has a special shape design, such as: circle, square, or a mesh matching a caliber of an ion mobility spectrometry.

An ion has a small charging amount, and therefore, a collection of the ions of the tracing sample would not be obviously affected during a short period of time. However, once the ion collecting and developing plate carries with the same charge as the charge of the ions, the ions are not enriched at a surface of the ion collecting and developing plate. Therefore, the ion collecting and developing plate carrying with the same charge as the charge of the ions should be avoided. During an actual process of this embodiment, with a receiving time less than 30 s, an enrichment degree of the particles is increased as time increases (a pattern on a plate gradually becomes brighter); this indicates that during this period of receiving time, the charge of the ions do no obviously affect, on the plate, collection of subsequent ions.

The foregoing content is a further description of the present application with reference to the specific/preferred implementations, and it cannot be deemed that the specific embodiment of the present application is limited the description only. A person of ordinary skill in the art may further make various replacements or modifications to the described embodiment without departing from the conception of the present application, and these replacement or modification means shall fall within the protection scope of the present application.

What is claimed is:

1. A method for tracing a distribution of moving ions in an ion mobility spectrometer, the method comprising the following steps:
    S1, selecting an ion sample: selecting a sample having light-emitting characteristics as a tracing sample of the ion mobility spectrometer, the light-emitting characteristics refer to an ability of a substance to release energy as light during a process of returning to a ground state from an excited state;
    S2, ionization sampling: ionizing the trace sample and feeding the ions of the tracing sample into a drift tube of an ion mobility spectrometer to be drifted;
    S3, ion collecting: placing an ion collecting and developing plate at a cross section to be detected, so as to capture the ions of the tracing sample drifted to the position of the cross section through the drift tube, the ion collecting and developing plate using a non-conductive material; and
    S4, developing: taking out the ion collecting and developing plate, performing a development on the collecting and development plate that includes illuminating, by using exciting light having an excitation wavelength of the ions of the tracing sample, the ions of the tracing sample to cause the ions of the tracing sample to emit light-emitting photons, the light emitted by the ions of the tracing sample forms a diagram of positions of the ions on a surface of the ion collecting and developing plate, and obtaining a position distribution of the ions of the tracing sample according to a light intensity distribution of the diagram.

2. The method for tracing a distribution of moving ions in an ion mobility spectrometer according to claim 1, wherein the light-emitting characteristics are laser-induced fluorescence.

3. The method for tracing a distribution of moving ions in an ion mobility spectrometer according to claim 1, wherein the trace sample is ionized in step S2 with one of an electrospray ionization source, an ultraviolet lamp ionization source, a matrix-assisted laser desorption ionization source, and a chemical ionization.

4. The method for tracing a distribution of moving ions in an ion mobility spectrometer according to claim 1, wherein the cross section in step S3 is a cross section to be analyzed of the drift tube of the ion mobility spectrometer that is perpendicular to a movement direction of the ions.

5. The method for tracing a distribution of moving ions in an ion mobility spectrometer according to claim 1, wherein the ion collecting and developing plate in step S3 refers to a plate which does not affect an electric field distribution of the ion mobility spectrometer, the plate comprising one of a paper plate, a glass plate, and a rubber plate.

6. The method for tracing a distribution of moving ions in an ion mobility spectrometer according to claim 1, wherein the ion collecting and developing plate in step S3 is a ion collecting and developing plate that fixes the ions and avoids diffused reflections of the ions, and the ion collecting and developing plate has one of a shape of circular, square, and mesh.

7. The method for tracing a distribution of moving ions in an ion mobility spectrometer according to claim 1, wherein the tracing sample in step S1 has one of fluorescent and phosphorescent characteristics.

* * * * *